US011202737B2

(12) United States Patent
Figueroa et al.

(10) Patent No.: US 11,202,737 B2
(45) Date of Patent: *Dec. 21, 2021

(54) CLEANSING COMPOSITIONS

(71) Applicant: Johnson & Johnson Consumer Inc., Skillman, NJ (US)

(72) Inventors: Jasmin Figueroa, Margate, FL (US); Diana Johnson, Hillsborough, NJ (US); Marcee Martinez, Skillman, NJ (US); Abhijit Bidaye, Edison, NJ (US); Farahdia Edouard, Edison, NJ (US)

(73) Assignee: Johnson & Johnson Consumer Inc., Skillman, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/146,005

(22) Filed: Jan. 11, 2021

(65) Prior Publication Data

US 2021/0128418 A1 May 6, 2021

Related U.S. Application Data

(63) Continuation of application No. 16/402,278, filed on May 3, 2019, now Pat. No. 11,039,990.

(60) Provisional application No. 62/667,019, filed on May 4, 2018.

(51) Int. Cl.
*A61K 8/02* (2006.01)
*A61K 8/31* (2006.01)
*A61K 8/36* (2006.01)
*A61K 8/37* (2006.01)
*A61K 8/60* (2006.01)
*A61K 8/81* (2006.01)
*A61Q 1/14* (2006.01)
*A61Q 19/00* (2006.01)
*A61K 8/34* (2006.01)

(52) U.S. Cl.
CPC .............. *A61K 8/0208* (2013.01); *A61K 8/31* (2013.01); *A61K 8/345* (2013.01); *A61K 8/361* (2013.01); *A61K 8/602* (2013.01); *A61K 8/8152* (2013.01); *A61Q 1/14* (2013.01); *A61K 2800/48* (2013.01); *A61K 2800/5922* (2013.01)

(58) Field of Classification Search
CPC ... A61K 8/02; A61K 8/31; A61K 8/34; A61K 8/36; A61K 8/37; A61K 8/60; A61K 8/81; A61Q 1/14; A61Q 19/00
See application file for complete search history.

(56) References Cited

U.S. PATENT DOCUMENTS

| | | | |
|---|---|---|---|
| 5,925,341 A | 7/1999 | Cervantes | |
| 6,221,817 B1 | 4/2001 | Guskey | |
| 6,242,396 B1 | 6/2001 | Guillou | |
| 6,342,469 B1 | 1/2002 | Lorant | |
| 6,352,963 B2 | 3/2002 | Ramin | |
| 6,419,946 B1 | 7/2002 | Sonneville | |
| 7,776,346 B2 | 8/2010 | O'Connor | |
| 8,795,692 B2 | 8/2014 | Hameyer | |
| 8,815,958 B2 | 8/2014 | Sasaki | |
| 9,095,528 B2 | 8/2015 | Desenne | |
| 9,387,160 B2 | 7/2016 | Oddos | |
| 9,707,415 B2 | 7/2017 | Desenne | |
| 9,862,853 B2 | 1/2018 | Tamor | |
| 9,872,832 B2 | 1/2018 | Wu | |
| 10,085,932 B2 | 10/2018 | Alves | |
| 10,335,362 B2 | 7/2019 | Sasaki | |
| 10,532,011 B2 | 1/2020 | Giron | |
| 10,660,866 B2 | 5/2020 | Parsa | |
| 10,682,303 B2 | 6/2020 | Fondin | |
| 11,039,990 B2* | 6/2021 | Figueroa | A61K 8/602 |
| 2003/0157047 A1 | 8/2003 | Lennon | |
| 2005/0261159 A1 | 11/2005 | Parris | |
| 2006/0099231 A1 | 5/2006 | De La Poterie | |
| 2006/0120983 A1 | 6/2006 | Blin | |
| 2007/0014744 A1 | 1/2007 | Swistowski | |
| 2008/0057008 A1 | 3/2008 | Naden | |
| 2008/0108709 A1 | 5/2008 | Meyer | |
| 2009/0074685 A1 | 3/2009 | Lai | |
| 2010/0137179 A1 | 6/2010 | Russell | |
| 2010/0161029 A1 | 6/2010 | Filippini | |
| 2010/0310486 A1 | 12/2010 | Blin | |
| 2012/0016024 A1 | 1/2012 | Ibe | |
| 2014/0170089 A1 | 6/2014 | Thaggard | |
| 2015/0038592 A1 | 2/2015 | Von Der Fecht | |
| 2016/0271023 A1 | 9/2016 | Bekemeier | |
| 2018/0200180 A1 | 7/2018 | Busscher | |
| 2018/0263890 A1 | 9/2018 | Clavel | |

(Continued)

FOREIGN PATENT DOCUMENTS

| | | |
|---|---|---|
| EP | 1106164 B1 | 2/2004 |
| EP | 1106165 B1 | 5/2004 |
| EP | 1680070 B1 | 4/2008 |
| EP | 1628627 B1 | 5/2008 |
| EP | 2134786 B1 | 7/2009 |
| EP | 1578392 B1 | 8/2010 |
| EP | 3090725 B1 | 11/2019 |
| FR | 3067248 B1 | 10/2019 |
| IN | 287205 B | 9/2017 |

(Continued)

OTHER PUBLICATIONS

Procter & Gamble China: GNPD—"Skincare Set", Jul. 1, 2013, XP055613484, Retrieved from the Internet: https://www.gnpd.com/sinatra/search_results/?&search_id=XyONer80iB&page=0&searchtype=products.

(Continued)

*Primary Examiner* — Brian P Mruk

(57) ABSTRACT

A cleansing composition and method of using a cleansing composition, the cleansing composition including a blend of three different emollients, the emollients including a first stearic ester, a second stearic ester, and a branched hydrocarbon, where the first stearic ester and second stearic ester are different from each other.

36 Claims, No Drawings

(56) References Cited

U.S. PATENT DOCUMENTS

| | | |
|---|---|---|
| 2019/0038527 A1 | 2/2019 | O'Connor |
| 2019/0240122 A1 | 8/2019 | Tadini D'Annolfo |
| 2019/0336407 A1 | 11/2019 | Figueroa |
| 2019/0365613 A1 | 12/2019 | Hwang |
| 2020/0060954 A1 | 2/2020 | King |
| 2020/0069542 A1 | 3/2020 | Debeaud |
| 2020/0138692 A1 | 5/2020 | Bichon |
| 2020/0188285 A1 | 6/2020 | Yamaki |

FOREIGN PATENT DOCUMENTS

| | | | | |
|---|---|---|---|---|
| JP | 05966642 B2 | | 8/2016 | |
| SG | 154912 A1 | | 9/2009 | |
| WO | WO 03/006009 | * | 1/2003 | ............. A61K 31/20 |
| WO | WO2003006009 A1 | | 1/2003 | |
| WO | WO 2006/020166 | * | 2/2006 | ............... A61K 7/48 |
| WO | WO2006020166 A1 | | 2/2006 | |
| WO | WO2013167866 A2 | | 11/2013 | |
| WO | WO2019211804 A1 | | 11/2019 | |

OTHER PUBLICATIONS

Anonymous: "Wrinkle Solution Cream", May 11, 2015, XP055613485, Retrieved from www.gnpd.com Database accession No. 3161521.

* cited by examiner

CLEANSING COMPOSITIONS

CROSS REFERENCE TO RELATED APPLICATIONS

This application is a continuation of prior U.S. application Ser. No. 16/402,278 filed May 3, 2019, now U.S. Pat. No. 11,039,990, which claims the benefit of U.S. Provisional Application Ser. No. 62/667,019 filed May 4, 2018. The complete disclosures of these applications are incorporated herein by reference for all purposes.

FIELD

The present invention relates to improved cleansing compositions, for use in cleansing skin surfaces. In particular, the invention is useful in cleansing the facial areas of the skin, and is particularly useful in cleansing various makeup products.

BACKGROUND

Because of the wide variety of skin, hair and nail problems faced by consumers, consumers have long sought personal care products which can cleanse the skin, or deliver and/or deposit benefit agents that alleviate such problems. A facial cleanser should desirably provide a suitable cleansing efficiency for removal of foundation, mascara and eyeliner. It is important, however, to avoid sacrificing the ability of products to adequately cleanse the skin in favor of reducing irritation to a user. Many delivery systems sacrifice aesthetics and cleaning ability in order to achieve stability and reduced irritation. This is particularly true when such products are to be used on sensitive areas, such as on the face, and even more particularly, in the very sensitive regions surrounding the eyes. It is also beneficial to provide a product that is pleasant feeling to the user, such as by having a more moisturized feel, with less greasiness, and lower levels of residue. Other features that are desirable include a higher cleansed feel and more softness (cushiony-feel) after use.

Accordingly, it would be desirable to create such a composition that is capable of cleansing the skin of a user adequately, where the composition has a low degree of ocular and skin irritation, and provides a pleasant after-feel.

SUMMARY

The present invention includes various cleansing compositions, and methods of using and preparing cleansing compositions. In one aspect, there is a cleansing composition including a fluid composition embedded into a substrate, where the fluid composition includes: a cleansing blend including a first stearic ester, a second stearic ester, and a branched hydrocarbon, where the first stearic ester and second stearic ester are different from each other. The compositions optionally include a blend of nonionic sucrose or glucose fatty acid esters. The compositions also optionally include a Carbomer Interpolymer thickener. In this aspect, the substrate includes a wipe or cloth, such as a nonwoven wipe.

In another aspect, the invention includes a cleansing composition including a fluid composition embedded into a substrate, where the fluid composition includes: a cleansing blend including a first stearic ester present in an amount of from about 1.0% to about 3.0% by weight of the fluid composition, a second stearic ester present in an amount of from about 1.0% to about 3.0% by weight of so the fluid composition, and a branched hydrocarbon present in an amount of from about 0.5% to about 1.5% by weight of the fluid composition, where the first stearic ester and second stearic ester are different from each other. The compositions optionally include a blend of nonionic sucrose or glucose fatty acid esters. The compositions also optionally include a Carbomer Interpolymer thickener. In this aspect, the substrate includes a wipe or cloth, such as a nonwoven wipe.

In other aspects, the invention includes a method of removing a cosmetic product from the skin of a user, including the steps of: first contacting the surface of the skin with a cleansing composition including a fluid composition embedded into a substrate, where the fluid composition includes: a cleansing blend including a first stearic ester, a second stearic ester, and a branched hydrocarbon, where the first stearic ester and second stearic ester are different from each other. The compositions optionally include a blend of nonionic sucrose or glucose fatty acid esters. The compositions also optionally include a Carbomer Interpolymer thickener. The method then includes the step of rubbing the surface of the skin with the substrate to remove at least a portion of the cosmetic product from the surface of the skin. In this aspect, the substrate includes a wipe or cloth, such as a nonwoven wipe. Cosmetic products include, for example, mascara, foundation, eyeliner, lipstick, and others.

DETAILED DESCRIPTION

The present invention provides compositions and materials that deliver optimal properties. As used herein, the term "optimal" includes comparable or improved cleansing efficacy when compared to known cleansers. Optimal does not necessarily mean 100% cleansing efficiency, but rather is a suitable efficiency to remove various cosmetics from the face. Efficient cleansing is described below in greater detail for various cosmetics. Other benefits provided by the cleaning compositions of the present invention may include one or more of the following: aesthetics, reduced greasiness, low irritation of skin and eyes, achieving shorter drying time with less force and lower cost, reducing the amount of cleansing agents in the composition, and enabling the cleaning compositions to be free of silicone. In some aspects, the cleansing compositions of the present invention are free of polyisobutenyl succinic anhydride derived emulsifiers or polyisobutylene derived emulsifiers.

As used herein, the term "percent" shall refer to the weight percent, and similarly, all amounts set forth herein shall be by weight unless noted otherwise. As also used herein, the term "water dispersible component" shall mean a material that produces a uniform, clear or hazy, mixture when combined with at least a weight equivalent of water. The term "benefit agent" used herein includes any active ingredient that is to be delivered into and/or onto the skin, hair or nail at a desired location, including but not limited to agents such as a cosmetic agent or a pharmaceutical agent. By "cosmetic agent," it is meant any ingredient that is appropriate for cosmetically treating, providing nutrients to, and/or conditioning the hair, nail, and/or skin via topical application. By "pharmaceutical agent," it is mean any drug that is appropriate for topical use. As used herein, "medicament agents" include those agents capable of promoting recovery from injury and illness.

Generally, the present invention includes cleaning compositions including one or more of the following: water, thickener(s), humectant(s), emollient(s), preservative(s), fragrance(s), excipient(s), extract(s), and buffer(s). Various combinations of the foregoing components are useful in the present invention. The compositions may be useful in liquid or gel form, to be applied by hand, or in combination with a wipe, sheet or sponge, so as to be applied by an applicator device.

The cleansing compositions useful in the present invention may be formulated comprising a combination of at least two emollients. As used herein, "emollients" refer to materials used for cleansing the skin, hair, and eye lashes, the prevention or relief of dryness, or for the protection of the skin. Examples of emollients include, but are not limited to, hydrophobic compounds such as vegetable oils, mineral oils (e.g., petrolatum), fatty esters (e.g., isopropyl palmitate, C12-C15 alkyl benzoate) including those fatty esters of glycerol and the like.

The cleansing compositions used herein include at least one oil phase and at least one water phase, and may include a plurality of oil phases in addition to a separate water phase. Each oil phase includes components described herein. When combined into a cleansing composition, the first oil phase, optional second so oil phase, and water phase provide a safe, effective, and pleasant cleanser. It is understood that in forming the cleansing composition, it is not necessary to separately form the first oil phase, second oil phase, and water phase, but rather the components in each of these phases may be added to each other in any desired arrangement. The designation of first oil phase, second oil phase, and water phase is intended to help explain and understand the components cleansing composition, but is not intended to designate any particular method or required steps used in forming the cleansing compositions described herein. Put another way, the first and second oil phases may be contained in one single oil phase.

The invention includes a fluid cleansing composition. The cleansing composition includes a first oil phase and a water phase, and optionally includes a second oil phase. As noted above, the first oil phase and the second oil phase may form one oil phase, and need not be formed separately. Further, all three phases need not necessarily be formed separately, and may be formed into a single batch or by addition of any components at any time. The identification of "phases" is merely intended to help describe the overall composition and is not necessarily intended to describe the formation of distinct and separately formed phases.

The first oil phase includes at least three emollients, where the first emollient, second emollient, and third emollients are each different from each other. The first emollient and the second emollient may be present in the same amount, or substantially the same amount. In some aspects, the first emollient may be present in an amount that is greater than the second emollient.

The first emollient may be an alkyl ester according to formula I:

$$R_1\text{-}R_2 \quad (I)$$

In the structure (I), $R_1$ is $C_3$ to $C_{22}$, and may be linear, branched, cyclic, saturated, or unsaturated. $R_1$ may have one, two, three, or four branching points. A branching point may have three bonds to other carbons and one to a hydrogen, or four bonds to other carbons. The side chains attached to a branching point may be methyl, ethyl, propyl, or butyl. Branching points may be at the end of $R_1$ (opposite to the ester group) or close to the ester group. Non-limiting examples include ethyl-hexyl, isopropyl, isopentyl, neopentyl, isohexyl, isodecyl, isododecyl, and the like. Examples of linear $R_1$ include propyl, hexyl, nonyl, decyl, and hexadecyl. $R_1$ may contain one or two groups with heteroatoms, such as oxygen, nitrogen, or sulfur, for example, hydroxy (—OH) and alkylether (—O-methyl, —O-ethyl and —O—$R_1$). $R_1$ may contain one, two, or three double bonds or triple bonds or both. $R_1$ may be synthetic, e.g. derived from petro-oil, or may be derived from renewable resources such as plant and animal material, such as triglyceride oils, or from fermentation processes, or may be derived from a mixture of resources.

$R_2$ is a carboxylic acid having the general structure: —O—CO—$R_3$. $R_3$ may have from about 12 carbons to about 22 carbons, and may be linear, branched, cyclic, saturated, or unsaturated. $R_3$ may have one, two, three, or four branching points. A branching point may have three bonds to other carbons and one to a hydrogen or four bonds to other carbons. The side chains attached to a branching point may be methyl, ethyl, propyl, or butyl. Branching points may be at the end of $R_3$ (opposite to the ester group) or close to the ester group. Examples of $R_2$ with branched $R_3$ include isododecanoate, isopentadecanoate, neopentadecanoate, isohexadecanoate, isobehenate, and the like. Examples of linear $R_2$ include e.g. laurate, myristate, stearate, behenate. $R_3$ may contain one or two groups with heteroatoms, such as oxygen, nitrogen, or sulfur, examples include hydroxy (—OH) and alkylether (—O-methyl, —O-ethyl and —O—$R_1$). Examples of $R_2$ with a hydroxy group in $R_3$ are alpha-hydroxy stearate, alpha-hydroxy palmitate, and ricinoleate. $R_2$ may contain one, two, or three double bonds or triple bonds or both. $R_2$ may be synthetic, e.g. derived from petro-oil, or may be derived from renewable resources such as plant and animal material like triglyceride oils, or from fermentation processes, or may be derived from a mixture of resources.

The first oil phase may also include a second emollient, and the second emollient may be an ester according to formula (I) above, where the second ester is different from the first ester. If $R_2$ differs by zero, one, or two carbons compared to $R_2$ of the first ester, $R_1$ of the second ester differs by at least five carbons compared to $R_1$ of the first ester. If $R_1$ differs by zero, one, or two carbons compared to $R_1$ of the first ester, $R_2$ of the second ester differs by at least five carbons compared to $R_2$ of the first ester.

The first emollient may be a stearic ester, such as an isostearate, and may include, for example, isopropyl isostearate, decyl isostearate, and hexyl isostearate. Isopropyl isostearate may be commercially available by its trade name Crodamol IPIS™. In some aspects, if decyl isostearate is used, it may be a simple ester produced using commercial isostearic acid or any of its derivatives useful to form esters. In some aspects, however, the decyl isostearate may be or include an isostearate that is formed from esterification of an isostearic acid or any of its derivatives useful to form esters, which has been subjected to a refining process to increase the proportion of mono-branched molecules present in the acid compared to non-refined (e.g., simple) acid. As used herein, the term "decyl isostearate" shall refer to a simple isostearate that has not been formed from a highly mono-branched acid, while the term "highly mono-branched decyl isostearate" refers to an ester formed from an isostearic acid having an increased proportion of mono-branched molecules compared to simple isostearic acid.

Thus, in some embodiments, the decyl isostearate may be a highly mono-branched decyl isostearate, which is formed from an isostearic acid having an increased proportion of mono-branched molecules compared to simple isostearic acid. A "highly mono-branched decyl isostearate" comprises a decyl isostearate wherein at least about 60% by weight of the molecules of decyl isostearate comprise a mono alkyl-branched isostearate group and less than about 25% by weight of the molecules of decyl isostearate comprise a poly alkyl-branched isostearate group. Exemplary highly mono-branched decyl isostearates, and methods of forming highly mono-branched decyl isostearates, may be found in U.S. Pat. No. 9,656,944, the contents of which are incorporated by reference herein in its entirety.

The first oil phase also includes a second emollient, where the second emollient is different than the first emollient. The second emollient may be an alkyl ester defined above, and further, the second emollient may be a second stearic ester, where the second stearic ester is different from the first stearic ester. Suitable stearic esters include those defined above with regard to the first stearic esters. By way of example, the first emollient may include isopropyl isostearate, and the second emollient may include a simple decyl isostearate and/or a highly mono-branched decyl isostearate. In some aspects, the second emollient may be a blend of simple decyl isostearate and highly mono-branched decyl isostearate. In embodiments where the first emollient and second emollient are a first stearic ester and a second stearic ester, the first stearic ester and the second stearic ester may be present in the same amount, or substantially the same amount. In some aspects, the first stearic ester may be present in an amount that is greater than the second stearic ester.

The first oil phase may also include a third emollient, where the third emollient is different than both the first and second emollients. The third emollient may also be an alkyl ester as defined above, or in some aspects, the third emollient may be a linear or branched chained hydrocarbon emollient having from 8 to 20 carbon atoms. Suitable linear or branched chained hydrocarbon emollients include, for example, decane, dodecane, tridecane, tetradecane, squalene, hexadecane, or isoparaffins. In certain aspects, the third emollient is a branched hydrocarbon emollient having from 10 to 20 carbon atoms, such as isohexadecane, which may be available under its trade name Permethyl 101A sold by Sumitomo Corporation.

If the third emollient is a branched hydrocarbon, it may optionally have from 1 to 5 branching points. A branching point may have three bonds to other carbons and one to a hydrogen or four bonds to other carbons. The side chains attached to a branching point may be methyl, ethyl, propyl, or butyl.

The third emollient may contain one or two groups with heteroatoms, such as oxygen, nitrogen, or sulfur, examples include hydroxy (—OH) and alkylether (—O-methyl, —O-ethyl and —O-propyl). $R_1$ may contain one, two, or three double bonds or triple bonds or both. The third emollient may be synthetic, e.g. derived from petro-oil, or may be derived from renewable resources such as plant and animal material like e.g. triglyceride oils, or from fermentation processes, or may be derived from a mixture of resources.

In certain aspects, the isohexadecane may have a structure according to formula II:

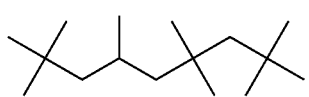

(II)

Desirably, each of the first and second emollients is independently present in an amount greater than the third emollient. By way of example, the first emollient may be present in an amount of about 0.5% to about 8% by weight of the composition or about 1% to about 6% by weight of the composition, and preferably about 2% to about 4% by weight of the composition; the second emollient may be present in an amount of about 0.5% to about 8% by weight of the composition or about 1% to about 6% by weight of the composition, and preferably about 2% to about 4% weight of the composition, and the third emollient may be present in an amount of about 0.5% to about 8% by weight of the composition or about 1% to about 6% by weight of the composition, and preferably about 2% to about 4% by weight of the composition.

It may be desired that the first emollient, second emollient, and third emollient be present in a desired ratio with respect to each other. By way of example, if the first emollient is a first stearic ester, the second emollient is a second stearic ester, and the third emollient is a branched hydrocarbon having from 8 to 20 carbon atoms, they may be present in a weight ratio of about 4:4:2, or about 2:2:1 (first stearic ester:second stearic ester:branched hydrocarbon).

In other aspects, the first emollient, the second emollient, and the third emollient may be present in approximately equal amounts by weight (e.g., about 1:1:1 weight ratio). However, depending upon the desired feel and cleansing desired, it may be preferable to modify the amounts of the three emollients. This may be particularly true when the other phases of the composition include certain components or have a particular skin feel profile. That is, the second oil phase and/or the water phase may include components that provide the overall composition with a desirable skin feel profile, and therefore the first oil phase may provide higher cleansing without the need to focus on desirable skin feel. By contrast, the second oil phase and/or the water phase may include components that do not provide the overall composition with a desirable skin feel profile, and therefore the first oil phase may focus more on a desirable skin feel while still providing a suitable cleansing profile.

While the emollients in the first oil phase are useful to provide cleansing, it is desirable that the overall cleansing composition of the present invention meet several criteria, including providing cleansing but also being low-greasy, high-so moisturizing, less residue, less tackiness and provide a more soft/cushiony feel for different makeup types including longwear/waterproof makeup.

For example, in some aspects it may be desirable to have the third emollient, such as a branched hydrocarbon, present in a weight amount lower than the first emollient and in an amount lower than the second emollient. In other embodiments, it may be desirable to have the third emollient, such as a branched hydrocarbon, present in an amount that is greater than one or both of the first emollient and the second emollient. Therefore, depending upon the components of the second oil phase and the water phase, the components in the first oil phase may be varied to suit the cleansing and skin feel profile of the overall composition.

Therefore, in some aspects, the ratios of the three emollients may be from about 1.1:1.1:1 (first stearic ester:second stearic ester:branched hydrocarbon) to about 2:2:1 (first stearic ester:second stearic ester:branched hydrocarbon). In other aspects, particularly where the third emollient is in an amount greater than the first and second emollients, respectively, the weight ratios of the three emollients may be from about 1:1:1.1 to about 1:1:3 or from about 1:1:1.3 to about 1:1:1.5 (first stearic ester:second stearic ester:branched hydrocarbon). The first oil phase is present in the composition in an amount of from about 2.5% to about 20% by weight of the overall cleansing composition, or about 5% to about 12% by weight of the overall cleansing composition, or about 7-10% by weight of the overall cleansing composition. It may be desired that the combined weight percentage of the first, second, and third emollients is about 7% by weight of the overall cleansing composition.

One emollient, di-PPG-3 myristyl ether adipate, may not provide the desired effects in the present invention. As such, it may be desired that the cleansing composition described and used herein is free of di-PPG-3 myristyl ether adipate.

The composition desirably includes a second oil phase. The second oil phase may include, for example, cleansing components such as humectants, nonionic surfactants (including non-foaming nonionic surfactants), glycerides, preservatives, fragrances, and the like.

The second oil phase may include one or more humectants, including aliphatic diols. Other commercially available humectants which are capable of providing moisturization and conditioning properties to the cleansing composition are suitable for use in the present invention. If present, the humectant is preferably present in an amount of from about 0.1 percent to about 4 percent, more preferably from about 0.5 percent to about 2 percent, and most preferably from about 0.5 percent to about 1 percent, based on the overall weight of the composition. Examples of suitable humectants nonexclusively include: 1) water soluble liquid polyols selected from the group comprising glycerine, propylene glycol, hexylene glycol, butylene glycol, pentylene glycol, dipropylene glycol, and mixtures thereof; 2) polyalkylene glycol of the formula III:

$$HO—(R''O)_b—H \quad (III)$$

wherein R" is an alkylene group having from about 2 to about 4 carbon atoms and b is an integer of from about 1 to about 10, such as PEG 4; 3) polyethylene glycol ether of methyl glucose of formula IV:

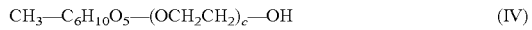

$$CH_3—C_6H_{10}O_5—(OCH_2CH_2)_c—OH \quad (IV)$$

wherein c is an integer from about 5 to about 25;
4) urea; 5) fructose; 6) glucose; 7) honey; 8) lactic acid; 9) maltose; 10) sodium glucuronate; and 11) mixtures thereof.

The second oil phase may also include one or more nonionic surfactants, including essentially non-foaming nonionic surfactants. An exemplary suitable essentially non-foaming ionic surfactant includes, for example, a blend of sucrose fatty acid esters. The blend of sucrose fatty acid esters may include sucrose combined with fatty acids such as stearic acid, lauric acid, myristic acid, oleic acid, palmitic acid, and combinations of one or more thereof. One such desirable blend of sucrose fatty acid esters is sucrose cocoate, which is commercially available under the trade name Tegosoft® LSE, available from Evonik Industries.

By "essentially non-foaming," it is meant that the surfactant, when used with the composition of the present invention, has a column height of less than about 20 mm as determined by the Ross-Miles Foam Generation Test. See 18 (I.) Oil & Soap 99-102 (1941) ("Ross-Miles Test"), which is incorporated by reference herein. The cleansing composition and the personal care system may either be rinseable with water or may be wiped-off. It is desired that any non-foaming nonionic surfactants used in cleansing compositions described herein be rinseable with water or require no rinsing at all. In some embodiments, it may be useful to use as the non-foaming nonionic surfactant a blend of sorbitan stearate and sucrose cocoate, available from Croda under the tradename, "Arlacel 2121." The non-foaming nonionic surfactant may be present in any desired amount, and in some aspects is present in an amount of from about 0.1% to about 2% by weight of the overall cleansing composition, or may be present in an amount of about 0.50% to about 0.75% by weight of the overall cleansing composition.

In addition to the emollients described above, the cleansing composition may include polymeric emulsifiers. Polymeric emulsifiers that may be useful include glycerides or triglycerides, including, for example, caprylic/capric triglyceride or PEG-6 caprylic/capric glyceride. As used herein, the term "polymeric emulsifier" shall mean those compounds capable of emulsifying systems whereby the polymeric emulsifiers have a molecular weight of at least about 5000, and preferably are block copolymers having a hydrophilic portion and a hydrophobic portion. When used at amounts effective for emulsifying the personal care system, the polymeric emulsifiers surprisingly do not cause significant eye sting, i.e., when the emulsifier-containing composition was used by 80 consumers in the eye area, no more than about 5% of such users expressed discomfort around the eye area. Other examples of suitable polymeric emulsifiers nonexclusively include polyethylene glycol-30 dipolyhydroxystearate available from Croda under the tradename "Cithrol DPHS;" dimethicone copolyol, which is available from Goldschmidt Chemical Corporation under the tradename, "Abil EM® 90"; substituted acrylates such as those available from The Goodrich Corporation under the tradename, "Pemulen®"; and mixtures thereof. The polymeric emulsifier(s) may be present in any desired amount, and in some aspects is present in an amount of from about 0.1% to about 2% by weight of the overall cleansing composition, or may be present in an amount of about 0.75% by weight of the overall cleansing composition.

The second oil phase may also include preservatives or preservative blends. Suitable preservatives include components such as ethylhexylglycerin, dehydroacetic acid, benzoic acid, phenoxyethanol, polyaminopropyl biguanide, chlorphenesin, PEG-4 Laurate, iodopropynyl butylcarbamate, and mixtures thereof. The preservative may be present in any desired amount, and in some embodiments, is present in an amount of from about 0.01% to about 2% by weight of the overall cleansing composition, or may be present in an amount of about 0.1 to about 1% by weight of the overall cleansing composition. In one aspect, the preservative blend includes chlorphenesin and phenoxyethanol.

The second oil phase may also include fragrances or fragrance blends. Fragrances may include essential oils, or aroma compounds, fixatives, extracts and vitamins and solvents. The fragrance may be present in any desired amount, and in some aspects is present in an amount of from about 0.01% to about 1% by weight of the overall cleansing composition, or may be present in an amount of about 0.1% to about 0.2% by weight of the overall cleansing composition.

The second oil phase is present in an amount of about 1% to about 10% by weight of the overall cleansing composition, or may be about 2.5% to about 5% by weight of the overall cleansing composition.

The first and second oil phases may be formed together to make one single oil phase, or they may be formed as separate components in the cleansing composition. The designation of a first and second oil phase is not intended to require the separate formation of these two oil phases. In processing the overall cleansing composition, it may be desired to process the two oil phases separately, or the two oil phases may be processed as a single phase with the order of addition of components being variable.

The composition includes a water phase. As with the first and second oil phases, the water phase need not necessarily be processed as a separate and distinct phase as the first and/or second oil phases. The water phase is present in the greatest amount as compared to the first and second oil phases, and may be present in an amount of from about 75% to about 95% by weight of the overall cleansing composition, or about 80% to about 85% by weight of the overall cleansing composition. The water phase includes water or another suitable carrier. The water may be present in amount of from about 75% to about 90% by weight of the final composition, and more desirably about 80% to about 88% by weight of the final composition.

The first oil phase, second oil phase, or the water phase may additionally include one or more thickeners, which may be hydrophilic thickeners. Examples of suitable hydrophilic thickeners nonexclusively include carbomers available from B.F. Goodrich under the tradename, "Carbopol® ETD 2020" (INCI: Acrylates/C10-C30 alkyl acrylate cross polymer), Carbopol® Ultrez 10 NF Polymer (INCI: Carbomer), acrylate copolymers and acrylate crosspolymers, hydroxyethylcellulose modified with cetyl ether groups available from Hercules under the tradename, "Natrosol® Plus", polyvinylmethyl ether/maleic anhydride (PVM/MA) decadiene crosspolymer available from International Specialty Products under the tradename, "Stabileze® QM," and copolymers and mixtures thereof, with carbomers being preferred. Examples of suitable acrylate copolymers nonexclusively include acrylate copolymers available from Rohm & Haas under the tradename, "Aculyn® 33," acrylates/aminoacrylates copolymer available from National Starch & Chemical Company under the tradename, "Structure Plus," acrylates/steareth-20 itaconate copolymer available from National Starch & Chemical Company under the tradename, "Structure 2001," acrylates/ceteth-20 itaconate copolymer available from National Starch & Chemical Company under the tradename, "Structure 3001," acrylates/steareth-20 methacrylate copolymer available from Rohm & Haas under the tradename, "Aculyn® 22," and copolymers and mixtures thereof. Carbopol ETD 2020 is referred to as a "carbomer interpolymer thickener", and is preferred in the present invention. The thickener may be present in an amount of about 0.05% to about 0.50% by weight of the overall cleansing composition, or from about 0.12% to about 0.18% by weight of the overall cleansing composition.

The water phase may also include a buffering agent. Suitable buffering agents may include, for example, such as citrate buffer, phosphate buffer, lactate buffer, gluconate buffer, and sodium hydroxide. The buffering agent or agents may be present in any amount desirable to achieve the desired pH. In some aspects, the buffering agent may be a blend of 20% sodium hydroxide and water or other solvent. The buffering agent may be present in an amount of about 0.01% to about 0.5% by weight of the final composition, and more desirably about 0.2% by weight of the overall cleansing composition.

In some aspects, the invention includes a cleansing composition that comprises or consists essentially of the first oil phase, the second oil phase, and the water phase. It is desired that the water phase be present in the greatest weight amount in the cleansing composition. It is also desired that the first oil phase be present in a weight amount that is greater than the second oil phase. The present invention may include a concentrated blend, in which the three phases are present but the amount of water is greatly reduced, where the concentrate may be prepared and maintained separately, with water added at a later date. The use of concentrates in this fashion may be particularly useful for manufacturing and shipping purposes, particularly where the final composition (with water) is prepared in a location separately from the other components.

The compositions described herein are useful in removing various cosmetic products from the skin of users, and in particular, are useful in removing mascara, foundation, lipstick and eyeliner efficiently and without a remaining heavy or greasy residue. Mascara is a notoriously difficult cosmetic material to remove from skin, as it deposits high levels of film formers and includes a relatively high level of hydrophobic materials. Further, mascara includes a high level of carbon dark pigments, giving it a dark color. In addition, since mascara is typically applied on the eyes or eyelashes, cleaning requires a gentle, low pressure and non-planar application. Eyeliner presents its own difficulties in removal, as it includes titanium dioxide, iron oxide, mica, silica and higher concentration of pigments/colorants, which may be more difficult to remove. In addition, as with mascara, eyeliner is often applied to the eyes or eye region, and cleansing requires a gentle, lower pressure and non-planar application. Foundation provides some difficulty as well, as it is typically an emulsion and may include silicones, which cause it to remain on the skin. Cosmetics today are geared towards a "24-hour" use, where the cosmetic remains on the skin of the user for an extended period of time. These "long-lasting" and waterproof cosmetics have a high transfer resistance, making them difficult to remove.

To provide a material that effectively and sufficiently removes enough of these three cosmetic materials is particularly desired. Further, it is desired to provide a composition that does not leave an oily or greasy residue on the surface of the skin, since such oily cleansers may be difficult to remove and leave the user with an unclean feeling. In addition, it is important that the cleansing composition provide low or no irritation to the skin, particularly the eyes. A soft and pleasant feel to the user's skin during and after use is also desired. The present invention provides a cleansing composition that has desirable characteristics defined herein, while providing suitable cleansing capabilities as well.

Another embodiment of the present invention is directed to a personal care system comprising, consisting, or consisting essentially of, based upon the total weight of the personal care system, a) a first oil phase; b) a second oil phase; and c) a water phase. The personal care system may be used as a liquid or gel composition, applied to the skin by the user's hands or other tool. Optionally, the personal care system may be soaked into or embedded into a substrate, such as a wipe or other application tool, where the user may simply remove the wipe or other application tool from a package and use the wipe or other application tool to achieve cleansing. In preferred embodiments, the cleansing composition is soaked into an individual wipe, and the user may use that wipe to cleanse the user's skin. Individual wipes may be packaged in a dispenser that includes a plurality of wipes, or may be packaged in a dispenser that includes only one wipe. Desirable substrates include wipes described in greater detail below.

The personal care system and cleansing composition may further optionally contain one or more benefit agents or pharmaceutically-acceptable salts thereof. As used herein, the term "benefit agent" includes any active ingredient that is to be delivered into and/or onto the skin, hair or nail at a desired location, such as a cosmetic agent or a pharmaceutical agent. By "cosmetic agent," it is meant any ingredient that is appropriate for cosmetically treating, providing nutrients to, and/or conditioning the hair, nail, and/or skin via topical application. By "pharmaceutical agent," it is mean any drug that is either hydrophobic or hydrophilic in nature and appropriate for topical use. As used herein "medicament agents" include those agents capable of promoting recovery from injury and illness. The benefit agent(s), if used, may be included in any of the first oil phase, the second oil phase, or the water phase, if compatible with the other components in the selected phase.

The benefit agents useful herein may be categorized by their therapeutic benefit or their postulated mode of action. However, it is to be understood that the benefit agents useful herein may, in some circumstances, provide more than one therapeutic benefit or operate via greater than one mode of action. Therefore, the particular classifications provided herein are made for the sake of convenience and are not intended to limit the benefit agents to the particular application(s) listed. In addition, the compounds, which are identified below as being suitable for use as benefit agents, may be used in an amount over and above the amount that they may be used for other purposes in the cleansing composition or personal care system.

Examples of suitable benefit agents include, but are not limited to, depigmentation agents; reflectants; film forming polymers; humectants; amino acids and their derivatives; antimicrobial agents; allergy inhibitors; anti-acne agents; anti-aging agents; anti-wrinkling agents, antiseptics; analgesics; antitussives; antipruritics; local anesthetics; anti-hair loss agents; hair growth promoting agents; hair growth inhibitor agents, antihistamines such as *Mandragora vernalis, Tanacetum parthenium* and the like; antiinfectives such as *Acacia catechu, Aloe barbadensis, Convallaria majalis, Echinacea, Eucalyptus, Mentha piperita, Rosa canina, Sassafras albidum*, and the like; inflammation inhibitors; anti-emetics; anticholinergics; vasoconstrictors; vasodilators; wound healing promoters; peptides, polypeptides and proteins; deodorants and anti-per spirants; medicament agents; skin emollients and skin moisturizers; skin firming agents, vitamins; tanning agents; skin lightening agents; antifungals such as *Centaurea cyanus, Kalmia latifolia* and antifungals for foot preparations; depilating agents; shaving preparations; external analgesics; perfumes; counterirritants; hemorrhoidals; insecticides; poison ivy products; poison oak products; burn products; anti-diaper rash agents; prickly heat agents; vitamins; amino acids and their derivatives; herbal extracts; retinoids; flavonoids; sensates; anti-oxidants; skin conditioners; hair lighteners, chelating agents; cell turnover enhancers; coloring agents; sunscreens, those active ingredients disclosed in U.S. Pat. No. 6,063,397, which is incorporated herein by reference, anti-edema agents, collagen enhancers, and mixtures thereof.

Examples of suitable anti-edema agents nonexclusively include bisabolol natural, synthetic bisabolol, and mixtures thereof.

Examples of suitable vasoconstrictors nonexclusively include horse chestnut extract, prickly ash, and mixtures thereof.

Examples of suitable anti-inflammatory agents nonexclusively include benoxaprofen, centella asiatica, bisabolol, feverfew (whole), feverfew (parthenolide free), green tea extract, green tea concentrate, hydrogen peroxide, lycopene including "Lyc-o-Pen" available from LycoRed Natural Products Industries, Ltd., oat oil, chamomile, and mixtures thereof.

Examples of collagen enhancers nonexclusively include vitamin A, vitamin C, and mixtures thereof.

Examples of suitable skin firming agent nonexclusively include dimethylaminoethanol ("DMAE").

Examples of suitable antipruritics and skin protectants nonexclusively include oatmeal, betaglucan, feverfew, soy and derivatives thereof, bicarbonate of soda, colloidal oatmeal, surfactant based colloidal oatmeal cleanser, *Anagallis arvensis, Oenothera biennis, Verbena officinalis*, and the like. These antipruritics may be used in an amount, based upon the total weight of the cleansing composition, from about 0.01 percent to about 40 percent, and preferably from about 1 percent to about 5 percent.

As used herein, colloidal oatmeal means the powder resulting from the grinding and further processing of whole oat grain meeting United States Standards for Number 1 or Number 2 oats. The colloidal oatmeal has a particle size distribution as follows: not more than 3 percent of the total particles exceed 150 micrometers in size and not more than 20 percent of the total particles exceed 75 micrometers in size. Examples of suitable colloidal oatmeals include, but are not limited to, "Tech-O" available from the Beacon Corporation and colloidal oatmeals available from Quaker.

Examples of suitable reflectants nonexclusively include mica, alumina, calcium silicate, glycol dioleate, glycol distearate, silica, sodium magnesium fluorosilicate, and mixtures thereof.

Suitable film forming acetyl tyrosinamide, zinc pyrithione, co al tar, benzoyl peroxide, selenium sulfide, hydrocortisone, sulfur, menthol, pramoxine hydrochloride, tricetylmonium chloride, polyquarternium 10, panthenol, panthenol triacetate, vitamin A and derivatives thereof, vitamin B and derivatives thereof, vitamin C and derivatives thereof, vitamin D and derivatives thereof, vitamin E and derivatives thereof, vitamin K and derivatives thereof, keratin, lysine, arginine, hydrolyzed wheat proteins, hydrolyzed silk proteins, octyl methoxycinnamate, oxybenzone, minoxidil, titanium dioxide, zinc dioxide, retinol, erthromycin, tretinoin, and mixtures thereof.

One type of benefit agent includes those therapeutic components that are effective in the treatment of dandruff, seborrheic dermatitis, and psoriasis as well as the symptoms associated therewith. Examples of such suitable benefits agents nonexclusively include zinc pyrithione, anthralin, shale oil and derivatives thereof such as sulfonated shale oil, selenium sulfide, sulfur; salicylic acid; coal tar; povidone-iodine, imidazoles such as ketoconazole, dichlorophenyl imidazolodioxalan, which is commercially available from Janssen Pharmaceutica, N.V., under the tradename, "Elubiol", clotrimazole, itraconazole, miconazole, climbazole, tioconazole, sulconazole, butoconazole, fluconazole, miconazole nitrate and any possible stereo isomers and derivatives thereof; piroctone olamine (Octopirox); selenium sulfide; ciclopirox olamine; anti-psoriasis agents such as vitamin D analogs, e.g. calcipotriol, calcitriol, and tacaleitrol; vitamin A analogs such as esters of vitamin A, e.g. vitamin A palmitate, retinoids, retinols, and retinoic acid; corticosteroids such as hydrocortisone, clobetasone, butyrate, clobetasol propionate and mixtures thereof.

The amount of benefit agent to be combined with the cleansing composition or the emulsion may vary depending upon, for example, the ability of the benefit agent to penetrate through the skin, hair or nail, the specific benefit agent chosen, the particular benefit desired, the sensitivity of the user to the benefit agent, the health condition, age, and skin, hair, and/or nail condition of the user, and the like. In sum, the benefit agent is used in a "safe and effective amount," which is an amount that is high enough to deliver a desired skin, hair or nail benefit or to modify a certain condition to be treated, but is low enough to avoid serious side effects, at a reasonable risk to benefit ratio within the scope of sound medical judgment. If included, a benefit agent may be present in the cleansing composition or personal care system in an amount, based upon the total weight of the composition/system, from about 0.01 percent to about 5.0 percent, and preferably from about 0.01 percent to about 2.0 percent, and more preferably from about 0.01 percent to about 1.0 percent.

Optionally, commercially available detergent thickeners that are capable of imparting the appropriate viscosity to conditioning compositions are suitable for use in this invention. If used, the detergent thickeners should be present in the compositions in an amount sufficient to raise the Brookfield viscosity of the composition to a value of between about 500 to about 10,000 centipoise. Examples of suitable detergent thickeners nonexclusively include: mono or diesters of polyethylene glycol of formula V.

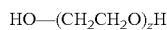

$$HO\text{---}(CH_2CH_2O)_z H \qquad (V)$$

wherein z is an integer from about 3 to about 200; fatty acids containing from about 16 to about 22 carbon atoms; fatty acid esters of ethoxylated polyols; ethoxylated derivatives of mono and diesters of fatty acids and glycerine; hydroxyalkyl cellulose; alkyl cellulose; hydroxyalkyl alkyl cellulose; and mixtures thereof. More specifically, suitable detergent thickeners nonexclusively include behenalkonium chloride; cetyl alcohol, quaternium-46, hydroxyethyl cellulose, cocodimonium chloride, polyquaternium-6, polyquaternium-7, quaternium-18, PEG-18 glycerol oleate/cocoate, a mixture of acrylates/steareth-50 acrylate copolymer, laureth-3 and propylene glycol, which is commercially available from Goldschmidt under the tradename "Antil 208," a mixture of cocamidopropylbetaine and glyceryl laurate which is commercially available from Goldschmidt under the tradename, "Antil HS60," a mixture of propylene glycol, PEG 55, and propylene glycol oleate, which is commercially available from Goldschmidt under the tradename, "Antil 414 liquid," and mixtures thereof. Preferred detergent thickeners include polyethylene glycol ester, and more preferably PEG-150 distearate which is available from the Stepan Company of Northfield, Ill. or from Comiel, S.p.A. of Bologna, Italy under the tradename, "PEG 6000 DS".

The above described cleansing composition may be prepared by combining the desired components in a suitable container and mixing them under any desired conditions in any conventional mixing means well known in the art, such as a mechanically stirred propeller, paddle, and the like. Processing may include the separate steps of forming the first oil phase, forming the second oil phase, and forming the water phase, followed by combining the first oil phase, second oil phase, and water phase together in any desired order to produce the final cleansing composition. Alternatively, the cleansing composition may be formed by forming the first and second oil phases as one single oil phase, where the order of addition of components is variable, and then that single oil phase be combined with the water phase, which is formed separately. Alternatively, the cleansing composition may be formed by combining the components in the first oil phase, the second oil phase, and the water phase together into a single composition, where the order of addition of components is variable.

The cleansing composition may be provided in a container in liquid, gel or cream form, whereby it may be applied to the skin by a user by hand or a cloth, wipe, sheet, or other device, or alternatively the composition may be embedded or soaked into one wipe or a plurality of sheets or wipes, whereby the composition may be applied to the skin by wiping the sheet, wipe, or other device.

Since the composition is to be applied to the face and is desirably used to remove cosmetic materials, it may be desired that the composition be soaked into a sheet or a wipe and provided to the user in this form. The user then removes the soaked wipe from a suitable air-tight package, and applies it directly to the skin. Thus, a system or package may include a plurality of wipes in a resealable package, where each wipe has been soaked in or otherwise contains a cleansing composition of the present invention. In other aspects, one individual wipe may be contained in its own air-tight package or container, where the package may be discarded after use of the wipe contained therein. The wipes are desirably disposable and include degradable components, rendering them environmentally friendly and sound. Wipe materials can include, for example, natural, biodegradable or synthetic fibers or filaments (e.g., wool, silk, jute, hemp, cotton, linen, sisal, or ramie) or synthetic (e.g., rayon, cellulose ester, polyvinyl derivatives, polyolefins, such as polyethylene and polypropylene, polyamides, such as nylon 6, nylon 6,6, or polyesters, such as polyethylene terephthalate and polybutylene terephthalate), or combinations thereof. These nonwoven materials are generally described in the INDA "NONWOVEN FABRICS HANDBOOK", (1999), for nonwoven substrates and their methods of manufacture. One particular substrate that may be useful is an embossed spunlace non-woven material made from a mixture of 20% Rayon 1.7 dtex, 40% Polyester (PET) 1.3 dtex and 40% Polyester (PET) 1.7 dtex. The basis weight of the substrate may vary, but generally ranges from about 20 grams per square meter to about 500 grams per square meter, for example from about 50 grams per square meter to about 150 grams per square meter. Wipe substrates may be any desired size, and in some aspects may have any desired area, including from about 2-10 inches in length and about 2-10 inches in width, more desirably about 7-8 inches in length and about 7-8 inches in width. Other suitable wipe materials include those described in EP 1 283 019 B1, U.S. Pat. No. 9,622,944 and US Patent Application No. 2016/0367102, the entire disclosures of each of which are incorporated by reference herein in their entireties.

In some aspects, the composition is provided to a user in a liquid dispensing bottle or container, where the user applies the composition onto a wipe or other applicator device, and the user uses that composition-applied applicator to cleanse the skin. The composition may be sold in a dispensing bottle by itself or may be sold in a kit wherein the package includes a dispensing bottle with the composition therein and a plurality of applicator devices, such as wipes or balls.

The present invention includes not only the cleansing composition described above, but also includes a method of using the cleansing composition described above. The method includes applying an effective amount of the composition to the skin, including facial skin and near ocular skin, and cleansing the skin with the composition. The composition may be applied to the skin by hand or through use of an applicator, such as a sheet, wet wipe, sponge, brush, and the like. The composition may be applied while the skin is wet or dry, and may be wiped off the skin, rinsed off the skin, or the skin may be allowed to dry after application of the composition. It is particularly desired that the composition be applied to the skin via a pre-soaked wipe and is allowed to dry off the skin without further washing or cleaning by the user. The used wipe may be disposed of by the user. The invention described herein may be practice in the absence of any component, ingredient or step not specifically disclosed herein or may include additional components or steps that are not expressly disclosed herein.

As noted above, the present invention is directed to compositions that can be used to clean a variety of cosmetics off of the surface of a user's skin effectively and efficiently. The inventive compositions should be capable of removing, for example, foundation, lipstick, eyeshadow, lipliner, eyebrow, pencil, pomade, blush mascara, concealer, highlighter and/or eyeliner efficiently. Further, the inventive compositions may be substantially free of silicones, if not entirely free of silicones.

The present invention may be better understood through the following examples, which are exemplary in nature and not intended to be limiting to any specific combination of elements.

EXAMPLES

The cleansing compositions and products described herein not only effectively remove desired makeup products from the skin, but also provide a number of beneficial characteristics to the user. Such desirable characteristics include, for example, leaving a low greasy feel on the applied skin, having a reduced or eliminated level of sting (such as eye sting), having a soft/cushiony feel, leaving a lower level of residue, and leaving the skin feeling moisturized.

The following nonlimiting examples demonstrate the effectiveness of the present invention.

Example 1—Neat Emollient Screening Tests

Each emollient was individually tested in vitro following the neat emollient screening instrument test Protocols, and was tested in vivo with the neat emollient screening phase protocols, detailed below. The neat emollients were screened to determine effectiveness based on efficacy of removing makeup (e.g. foundation, eyeliner and mascara), skin feel and cost. As used herein, the term "neat" refers to a sample including the emollient by itself without other added components. The "neat" emollient test may include the emollient embedded into or dispersed onto/into a wipe substrate, as described below.

Example 1A—Neat Emollient Screening In Vitro Tests

Each emollient was tested in vitro to determine the cleansing efficacy of removal of foundation (Revlon ColorStay™ Foundation 450 Mocha), eyeliner (L'Oréal Paris Infallible Never Fail Eyeliner, Black 511), and mascara (CoverGirl LashBlast Fusion Water Resistant Mascara 885 very back).

The in vitro test was carried out with a Sheen Wet Abrasion Scrub Tester (REF 903/PG) and X-rite Spectrophotometer (Hunter Labscan XE) following the protocol as described below, followed by a Tukey-Kramer Colorimetric Assessment (measuring delta E).

1. Prepared four silicone strips for each emollient sample
2. Applied each make-up formulations to a 4 cm×2 cm rectangle area on its individual silicone strip (one make-up formulation per silicone strip) and left to dry overnight
3. Placed 400 g weights on Sheen Wet Abrasion Scrub Tester and wipe the materials attached
4. Took readings of the silicone strips after drying overnight using the spectrophotometer to set a baseline color level.
5. Applied 500 microliter emollient onto the applied make-up on the silicone strip, and spread across the area (back and forth) using a finger cot for 15 seconds
6. Applied 500 microliter emollient onto wipe material, an embossed spunlace non-woven material made from a mixture of 20% Rayon 1.7 dtex, 40% Polyester (PET) 1.3 dtex and 40% Polyester (PET) 1.7 dtex (this resulting wipe is referred to as the "sample substrate")
7. Performed a scrub test for each sample by rubbing the emollient-embedded sample substrate across the sample for a predetermined number of passes:
   a. Foundation: 5 passes
   b. Eyeliner: 3 passes
   c. Mascara: 30 passes
8. Took a reading of each silicone strip after the scrub test using the spectrophotometer and determining the resulting color level. The net change of the color measured between the first spectrophotometer reading and the second spectrophotometer reading is referred to as "Delta E".

Example 1B—Neat Emollient Screening In Vivo Tests

Each emollient was also tested in vivo for efficacy of removal of foundation (Revlon ColorStay™ Foundation 450 Mocha), eyeliner (L'Oréal Paris Infallible Never Fail Eyeliner, Black 511), and mascara (CoverGirl LashBlast Fusion Water Resistant Mascara 885 very black).

The in vivo general test procedure employs a protocol which can be described as follows:
Two panels of human individuals were used: P1 and P2
Drew three 1" circles 1.5" apart on the two panel's volar forearm
Applied make-up formulations to the circles (0.001 g foundation, 0.002 g eyeliner and 0.015 g mascara) and allowed to dry for 45 minutes
Took a Picture of the unwiped soiled circle
Applied approximately 0.015-0.020 g neat emollient and wiped with an embossed sample substrate back and forth for 15 seconds
Wiped once with a cotton pad and took picture of the wiped circle
Wiped second time with clean area of cotton pad and took a second picture of the wiped circle
The panelists were asked to rank the top 5 samples from 1-5 for cleansing efficacy, where a ranking of 1 was considered the most effective cleansing product, and a ranking of 5 was considered the least effective cleansing product, below the top five they were not rated.

Following the In vitro and in vivo procedures described above, several neat emollients were tested for their cleansing efficacy; Table 1 below sets forth the results of such In Vitro and In Vivo test result. It is noted the combination of PEG-20 glyceryl triisostearate & isohexadecane was not tested in vivo since it was determined that PEG-20 Glyceryl Triisostearate does not contribute to makeup removal when evaluated as a single emollient. In addition, Polymeric ester (sold as ModiSurf Lift by Croda) was not tested in vitro due to its primary application in the home care and household space. PPG-3 benzyl ether ethylhexanoate was tested further in a separate consumer study, however, this composition was not pursued further.

TABLE 1

Neat Emollient Efficacy Screening Results

| Emollient name | In vitro (Net change in Delta E) | | | In vivo (subjective) | | |
|---|---|---|---|---|---|---|
| | Foundation | Eyeliner | Mascara | Foundation | Eyeliner | mascara |
| PEG-20 Glyceryl Triisostearate + Isohexadecane | −14.66 | −15.06 | −0.325 | | | |
| Isopropyl Isostearate | −14.31 | −15.84 | −0.38 | 4 | | 2 |
| Isohexadecane | −10.69 | −13.98 | −1.4 | 3 | 2 | 1 |
| Decyl Isostearate (and) Isostearyl Isostearate | −3.65 | −14.46 | −0.375 | | | |
| PPG-3 Isostearyl Methyl Ether | −10.99 | −13.61 | 0.02 | 1 | | |
| PPG-3 Benzyl Ether Myristate | −3.07 | −4.95 | −0.1 | | 4 | |
| PPG-3 Benzyl Ether Ethylhexanoate | −0.24 | −11.07 | −0.24 | 2 | 5 | 5 |
| Di-PPG-2 Myreth-10 Adipate | 1.93 | −11.75 | 0.3 | | 3 | |
| Di-PPG-3 Myristyl Ether Adipate | −0.59 | −1.01 | 0.165 | 1 | | |
| Diisocetyl Dodecanedioate | | | | | 4 | |
| Polymeric ester | | | | | 5 | 3 |

The tests above illustrated that Isopropyl Isostearate, Isohexadecane, and Decyl Isostearate (deblended Decyl Isostearate (and) Isostearyl Isostearate) consistently performed well in cleansing efficacy and exhibited good skin feel. Based on the promising test results, these three emollients were selected as the leading basic neat emollients for further testing, described below.

Example 2—Neat Emollient Blend Tests

Various emollients were blended together in equivalent ratios (1:1:1 by weight of active emollient) and tested for cleansing efficacy and skin feel. The emollients tested, in various blends, included Isopropyl Isostearate (sold as Crodamol™ IPIS), Diisostearyl Adipate (sold as Liquiwax™ DISA), PPG-3 Isostearyl Methyl Ether (sold as Arlamol™ LST), PPG-3 Benzyl Ether Ethylhexanoate (sold as Crodamol™ SFX), Decyl Isostearate (and) Isostearyl Isostearate (sold as Crodamol™ SSA), PPG-3 Benzyl Ether Myristate (sold as Crodamol™ STS), Di-PPG-3 Myristyl Ether Adipate (sold as Cromollient™ DP3-A), Dioctyldodecyl Dodecanedioate (sold as Liquiwax™ DIADD).

Various emollient blends were tested in vitro and in vivo to determine the efficacy of removal of foundation (Revlon ColorStay™ Foundation 450 Mocha), eyeliner (L'Oréal Paris Infallible Never Fail Eyeliner, Black 511), and mascara (CoverGirl LashBlast Fashion Water Resistant Mascara 885 very black). The in vivo tests conducted follow the procedures outlined in Example 1 above. The blend efficacy results are set forth in Table 2 below.

TABLE 2

Neat Emollient Blend Efficacy Screening Results

| Emollient Blend | In vitro (Net change in Delta E) | | In vivo (subjective) | |
|---|---|---|---|---|
| | Foundation | Mascara | Foundation | Mascara |
| Crodamol ™ IPIS + Liquiwax ™ DISA + Crodamol ™ STS | 9.7 | 10.3 | Scored #1 and #2 with 2 panelists | Scored #1 with 1 panelist, #2 with another panelist, other 2 panelists bottom 5 |
| Crodamol ™ IPIS + Liquiwax ™ DIADD + Liquiwax ™ DISA | 9.3 | 11.3 | Scored in bottom 5 | Scored in top 5 with 3 panelists |
| Crodamol ™ IPIS + Liquiwax ™ DIADD + Crodamol ™ STS | 10.4 | 12.3 | Scored #1 with 2 panelists | Scored in top 5 with 2, and bottom 5 with 2 |
| Crodamol ™ IPIS + Cromollient ™ DP3-A + Liquiwax ™ DISA | 9.6 | 13 | Top 5 with 3 panelists | Top 5 with 3 panelists |
| Crodamol ™ IPIS + Liquiwax ™ DIADD + Cromollient ™ DP3-A | 9.2 | 10.5 | Top 5 with 2 panelists | Bottom 3 with 3 panelists |
| Crodamol ™ IPIS + Cromollient ™ DP3-A + Crodamol ™ STS | 10.5 | 8.4 | Top 5 with 2 panelists | Bottom 5 with all 4 panelists |
| Liquiwax ™ DIADD + Liquiwax ™ DISA + Crodamol STS | 6.9 | 8.9 | Average to bottom with all 4 panelists | Average, 1 panelist put it in the top 5 |

TABLE 2-continued

Neat Emollient Blend Efficacy Screening Results

| Emollient Blend | In vitro (Net change in Delta E) | | In vivo (subjective) | |
|---|---|---|---|---|
| | Foundation | Mascara | Foundation | Mascara |
| Liquiwax ™ DIADD + Cromollient ™ DP3-A + Liquiwax ™ DISA | 8.2 | 12.5 | Bottom 5 with all 4 panelists | Top choice with 1 panelist, all others in the bottom 5 |
| Cromollient ™ DP3-A + Liquiwax ™ DISA + Crodamol ™ STS | 8.7 | 9.9 | Bottom 5 with all 4 panelists | Top 5 with 2 panelists, bottom 5 with 2 panelists |
| Liquiwax ™ DIADD + Cromollient ™ DP3-A + Crodamol ™ STS | 8.3 | 8.9 | Top choice with 1 panelist, bottom 5 with all other panelists | Middle to bottom 5 with all panelists |
| Crodamol ™ IPIS + Arlamol ™ LST + Crodamol ™ SSA | 13 | 13.5 | performed bottom 4 for foundation; 2 were top 5; 2 were bottom 5 | 3 out of 4 ranked blend at bottom 5 ranked in bottom 5 for mascara |
| Crodamol ™ IPIS + Crodamol ™ SFX + Arlamol LST | 14.5 | 14.5 | | |
| Crodamol ™ IPIS + Liquiwax ™ DISA + Arlamol ™ LST | 14.2 | 15.3 | 3 panelists ranked it in top 3; 1 ranked it in last place | 3 ranked it in bottom 5 for mascara; 1 ranked it in top 4 for mascara |
| Crodamol ™ IPIS + Liquiwax ™ DIADD + Arlamol ™ LST | 11.6 | 13.2 | 3 ranked in bottom 5; 1 ranked in top 4 | 2 ranked in top 4; 2 ranked in bottom 5 |
| Crodamol ™ IPIS + Liquiwax ™ DIADD + Crodamol SFX | 14 | 16.3 | all ranked in top 4 | 3 ranked in bottom 5; 1 ranked in top 4 |
| Crodamol ™ IPIS + Liquiwax ™ DISA + Crodamol ™ SFX | 13.6 | 15.8 | 2 ranked in top 4; 2 ranked in bottom 5 | 2 ranked in top 4; 2 ranked in bottom 5 |
| Crodamol ™ IPIS + Crodamol ™ SSA + Crodamol ™ SFX | 14.6 | 16.6 | 3 ranked in top 4; 1 ranked in bottom 5 | 3 ranked in top 4; 1 ranked in bottom 5 |
| Crodamol ™ IPIS + Crodamol ™ STS + Arlamol ™ LST | 14.2 | 15.7 | 1 ranked in top 4; 3 ranked in bottom 5 | 3 ranked in top 4; 1 ranked in bottom 5 |
| Crodamol ™ IPIS + Crodamol ™ STS + Crodamol ™ SFX | 14.6 | 15.2 | all ranked in bottom 5 | 2 ranked in top 4; 2 ranked in bottom 5 |
| Crodamol ™ IPIS + Liquiwax ™ DISA + Crodamol ™ STS | 9.7 | 10.3 | Scored #1 and #2 with 2 panelists | Scored #1 with 1 panelist, #2 with another panelist, other 2 panelists bottom 5 |

Based upon the in vivo and in vitro tests conducted, Liquiwax™ DISA was not continued due to lower cleansing efficacy against foundation and powder, and in addition to a perceived greasy feel. Liquiwax™ DIADD was not continued due to performance against foundation. Crodamol™ STS and Liquiwax™ DIADD were not continued due to performance against mascara. Cromollient™ DP3-A was not continued due to a greasy skin feel. Arlamol™ LST was not continued due to performance against mascara.

The neat emollient blend of Crodamol™ IPIS+Crodamol™ SSA+Crodamol™ SFX (i.e. Isopropyl Isostearate+Isostearyl Isostearate+PPG-3 Benzyl Ether Ethylhexanoate) was selected as the leading emlient blend for additional formulation testing, as it exhibited a Net change Delta E value of 14.6 and 16.6 in foundation and mascara, respectively in In vitro test; and three panelists scored it #1 with only one panelist scoring it in bottom 5 in two separate in vivo foundation and mascara tests.

Example 3: Compositions Including Varying Emollient Blends

To determine the cleansing efficacy of emollient-containing compositions, various compositions were prepared. Each composition included (i) a water phase, (ii) a first oil phase containing the emollient blends, and (iii) a second oil phase. Each composition was prepared and was tested for removal of various makeup cosmetics (foundation (Revlon ColorStay™ Foundation 450 Mocha), eyeliner (L'Oréal Paris Infallible Never Fail Eyeliner, Black 511), and mascara (CoverGirl LashBlast Fushion Water Resistant Mascara 885 very black).

The tested formulations were prepared and were impregnated into sample substrate wipes, the sample substrate being described above. The formulations were dosed at 3.7 g of lotion per g of substrate wipe. The tested formulations are set forth in Table 3A below.

TABLE 3A

Compositions of Varying Emollient Blends in First Oil Phase

| Component | Example 1 | Example 2 | Example 3 | Example 4 | Example 5 | Example 6 |
|---|---|---|---|---|---|---|
| Water | QS | QS | QS | QS | QS | QS |
| Emulsifiers | 1.05 | 1.05 | 1.05 | 1.05 | 1.05 | 1.05 |
| Preservatives | 0.7 | 0.7 | 0.7 | 0.7 | 0.7 | 0.7 |
| Sodium Hydroxide | 0.18 | 0.18 | 0.18 | 0.18 | 0.18 | 0.18 |
| Hexylene Glycol | 1.0 | 1.0 | 1.0 | 1.0 | 1.0 | 1.0 |
| PEG-6 Caprylic Capric Glycerides | 0.75 | 0.75 | 0.75 | 0.75 | 0.75 | 0.75 |
| Isopropyl Isostearate | 3.34 | 5.00 | 3.34 | 5.00 | — | 3.34 |
| Di-PPG-3 Myristyl Ether Adipate | 3.33 | 2.5 | — | — | 5.00 | 3.33 |
| Diisostearyl Adipate | 3.33 | 2.5 | — | — | — | 3.33 |
| Decyl Isostearate (and) Isostearyl Isostearate | — | — | 3.33 | 2.5 | — | — |
| PPG-3 Benzyl Ether Ethylhexanoate | — | — | 3.33 | 2.5 | 2.5 | 2.5 |
| PPG-3 Isostearyl Methyl Ether | — | — | — | — | 2.5 | 2.5 |
| Isopropyl Myristate | — | — | — | — | — | 1.0 |

The wipes were then evaluated by two panels of human subjects, following the procedures as described below:
Drew three 1" circles 1.5" apart on the two panel's volar forearm Applied make-up formulations to the circles (0.001 g foundation, 0.002 g eyeliner and 0.015 g mascara) and allowed to dry for 45 minutes Each sample substrate-impregnated wipe (Example 1-Example 6) was prepared and was provided to the subjects.

Panelists were asked to wipe the area 3 times with the wipe and evaluate the samples individually. Each sample was ranked with scores from 1-7, where a score of 1 is the best or most desirable wipe composition, and a score of 7 is considered the least desirable wipe composition.

TABLE 3B

In Vivo Efficacy Test of Compositions

| Composition | Panel 1 In-Vivo Efficacy Test (subjective visual assessment) | Panel 2 In-Vivo Efficacy Test (subjective visual assessment) |
| --- | --- | --- |
| Example 1 | 4 | 6 |
| Example 2 | 5 | 3 |
| Example 3 | 1 | 1 |
| Example 4 | 2 | 4 |
| Example 5 | 3 | 1 |
| Example 6 | 7 | 7 |

Examples 1, 2 and 4-6 were deemed to not meet optimal cleansing efficacy based on the panel data above. Although Example 3 exhibited sufficient cleansing efficacy and was ranked and scored #1, due to global requirements this formulation was not pursued further.

The present inventors also tested the individual ingredients of Crodamol™ SSA, and it was determined that the decyl isostearate in Crodamol™ SSA had increased effectiveness in cleansing efficacy against makeup. Finally, based upon the examples described herein, isohexadecane was chosen to further test, based on its ability to remove mascara as shown in the "neat" emollient tests above.

Example 4: Compositions of Varying Ratios of Components

Based upon the results of the neat and composition tests above, further compositions were tested for efficacy. In particular, different ratios of emollients were tested to determine whether makeup removal and/or other skin-feel criteria were affected by the ratios of components. The compositions were prepared as described in Table 4A below. The ratios provided in the table refer to weight ratios of the three emollients set forth in the table.

TABLE 4A

Emollient System for First Oil Phase

| Component | Emollient Blend |
| --- | --- |
| Emollient Blend 7 | Isopropyl Isostearate (IPIS):Decyl isostearate or Highly Mono-Branched Decyl Isostearate (DIS):Tween-20 (2:2:1) |
| Emollient Blend 8 | Isopropyl Isostearate(IPIS):Decyl isostearate or Highly Mono-Branched Decyl Isostearate (DIS): Isohexadecane (IHD) (2:0:1) |
| Emollient Blend 9 | Isopropyl Isostearate(IPIS):Decyl isostearate or Highly Mono-Branched Decyl Isostearate (DIS):Di-PPG-3 Myristyl Ether Adipate (DP3A) (1:1:1) |

TABLE 4A-continued

Emollient System for First Oil Phase

| Component | Emollient Blend |
| --- | --- |
| Emollient Blend 10 | Isopropyl Isostearate(IPIS):Decyl isostearate or Highly Mono-Branched Decyl Isostearate (DIS): Isohexadecane (IHD) (2:2:1) |
| Emollient Blend 11 | Isopropyl Isostearate(IPIS):Decyl isostearate or Highly Mono-Branched Decyl Isostearate (DIS):Di-PPG-3 Myristyl Ether Adipate (DP3A) (2:2:1) |
| Emollient Blend 12 | Isopropyl Isostearate(IPIS):Decyl isostearate or Highly Mono-Branched Decyl Isostearate (DIS): Isohexadecane (IHD) (2:2:1) |
| Emollient Blend 13 | Isopropyl Isostearate(IPIS):Decyl isostearate or Highly Mono-Branched Decyl Isostearate (DIS): Isohexadecane (IHD) (1:1:1.4) |

Each composition was prepared and included (i) a water phase, (ii) a first oil phase containing the emollient blends, and (iii) a second oil phase. The first oil phase includes a combination of three emollients, as described in the Table 4A above.

Table 4B and Table 4C below show exemplary component levels of the second oil phase and the water phase, respectively. The amount of the second oil phase and the water phase may vary depending upon the desired composition.

TABLE 4B

Exemplary levels of second oil phase components

| Component | Amount (weight percent of final composition) |
| --- | --- |
| Hexylene Glycol | 1.00-2.00 |
| Sucrose Cocoate | 0.5-1.25 |
| Chlorphenesin | 0.25-0.50 |
| PEG-6 Caprylic/Capric Glycerides | 0.75-3.00 |
| Phenoxyethanol | 0.40-0.75 |
| Fragrance | 0.06-1.00 |

TABLE 4C

Exemplary water phase

| Component | Amount (weight percent of final composition) |
| --- | --- |
| Water | 80-90 |
| Acylates/C10-C30 Alkyl Acrylate Cross Polymer | 0.10-0.25 |
| Water, Sodium Hydroxide | 0.10-0.25 |

Examples 7-14 as set forth in Table 4A were prepared, including the three phases of components described in Tables 4A, 4B and 4C. The formulations tested are set forth in Table 4D below.

TABLE 4D

Compositions of Varying Ratios of Components

| Component | Example 7 | Example 8 | Example 9 | Example 10 | Example 11 | Example 12 | Example 13 | Example 14 |
|---|---|---|---|---|---|---|---|---|
| Water | QS | QS | QS | QS | QS | QS | QS | QS |
| Emulsifiers | 1.05 | 1.05 | 1.05 | 1.05 | 1.05 | 1.05 | 1.05 | 1.05 |
| Preservatives | 0.77 | 0.77 | 0.77 | 0.77 | 0.77 | 0.77 | 0.77 | 0.77 |
| Sodium Hydroxide | 0.18 | 0.18 | 0.18 | 0.18 | 0.18 | 0.18 | 0.18 | 0.18 |
| Hexylene Glycol | 1.0 | 1.0 | 1.0 | 1.0 | 1.0 | 1.0 | 1.0 | 1.0 |
| PEG-6 Caprylic Capric Glycerides | 0.75 | 0.75 | 0.75 | 0.75 | 0.75 | 0.75 | 0.75 | 1.50 |
| Isopropyl Isostearate | 4.0 | 6.60 | 3.33 | 3.33 | 1.67 | 4.0 | 4.0 | 2.8 |
| Decyl Isostearate | 4.0 | — | 3.33 | 3.33 | 1.67 | 4.0 | 4.0 | 2.8 |
| Isohexadecane | — | 3.40 | — | 3.33 | 6.68 | — | 2.0 | 3.4 |
| Tween-20 | 2.0 | — | — | — | — | — | — | — |
| Di-PPG-3 Myristyl Ether Adipate | — | — | 3.33 | — | — | 2.0 | — | — |

The compositions set forth in Table 4D were prepared and were tested for in vitro cleansing ability. Also tested was a comparative sample, which included the cleansing composition that is included in commercially-available silicone containing cleanser (Neutrogena™ Makeup Removing Cleanser Towelettes). Four runs were conducted for each composition. White, high density polypropylene (HDPP) chips were dosed different makeup samples, either with 0.015 g of either Revlon Colorstay 450 Mocha foundation or 0.015 g of Hydro Boost Waterproof Mascara Black. The makeup was applied to a 1-inch round diameter area. The makeup dried for 1 hour.

The oil phases were combined to each other separately from the water phase, with each phase being blended at room temperature. The water phase was blended until homogenized. Once homogenized, the water phase was added to the oil phase and the resulting combination was mixed together.

For each composition including the comparative composition, a sample substrate (defined above). Each sample substrate wipe, measuring 7.2×7.4 inches, was wetted by adding 3.7 g of formula per gram of fabric. The wetted wipes were placed on a 50 g weighted sled attached to an Instron instrument (Instr-Met Corporation, IM 1122_4585). The test settings of the Instron instrument were: Number of cycles: 4, 50 in per min, Endpoint 1: 6.0, Endpoint 2: 0.0, Hold time: 3 seconds.

Images were taken with a Nikon camera (Nikon D800 with a AF-Micro NIKKOR 60 mm 1:28 GED lens) at a fixed distance of 7.3 inches with a X-Pol filter. Images were taken (i) before applying makeup, (ii) after applying makeup, and (iii) after makeup removal. The images were analyzed using Matlab calculating the change in LAB values between baseline, after adding makeup, and after makeup removal from the center of the circle of applied makeup. The percentage of makeup removal was calculated for each chip and set forth in Table 5 below. It is noted that the comparative sample was run several times, as was Example 13, and the various results are reported below.

TABLE 5

Varying Emollient Ratio Tests

| Formula | Emollients: | Emollient Ratio: | Mascara | Eyeliner | Foundation |
|---|---|---|---|---|---|
| Comparative | Silicone-containing Cleanser | | 80.7 | 62.8 | 77.5 |
| Example 9 | IPIS:DIS:DP3A | 1:1:1 | 65.3 | 41.1 | 55.6 |
| Example 12 | IPIS:DIS:DP3A | 2:2:1 | 58.6 | 37.7 | 51.8 |
| Comparative | Silicone-containing Cleanser | | 80.2 | 60.2 | 82.2 |
| Example 13 | IPIS:DIS:IHD | 2:2:1 | 76.9 | 56.4 | 76.4 |
| Comparative | Silicone-containing Cleanser | | 91.9 | 65.0 | 69.9 |
| Example 13 | IPIS:DIS:IHD | 2:2:1 | 90.3 | 56.7 | 82.1 |
| Example 7 | IPIS:DIS:T20 | 2:2:1 | 73.1 | 54.1 | 58.2 |
| Comparative | Silicone-containing Cleanser | | 88.6 | 74.5 | 79.6 |
| Example 8 | IPIS:DIS:IHD | 2:0:1 | 91.5 | 76.5 | 94 |
| Example 11 | IPIS:DIS:IHD | 1:1:4 | 86.1 | 85.1 | 95.1 |
| Example 10 | IPIS:DIS:IHD | 1:1:1 | 89.5 | 83.9 | 92.6 |
| Comparative | Silicone-containing Cleanser | | 90.6 | 45.5 | 91.3 |
| Example 14 | IPIS:DIS:IHD | 1:1:1.4 | 93.0 | 57.4 | 97.5 |

As shown in the In vitro measurement for cleansing efficacy tests above, Example 13 scored either statistically equivalently or exceeded to the commercially available silicone containing cleanser. Example 13 was determined to be the most effective cleansing system.

Example 5: Further Composition Modifications

Example 13 above was deemed to be promising, and to this formulation a few modifications were made and tested for efficacy and to determine impact of several modifications. The results of these modified formulations are set forth herein.

Example 13 was prepared, with the modification that Hexylene glycol and glycerox 767 were removed therefrom. The resulting composition was tested in vitro (using the method described in Example 1) to determine makeup removal efficacy. It was determined that the resulting composition decreased makeup removal efficacy.

Example 13 was prepared, with the modification that Glycerox 767 was increased to a level of 3% by weight of the composition. This modification was found to increase makeup removal efficacy against foundation, however it was found to increase greasy skin feel and overall cost of the cleansing composition.

Example 13 was prepared, with the modification that Tween 20 was added at a level of 0.25%. it was found that addition of this component increased the formulation stability.

Example 13 was prepared, with the modification that the total amount of emollients was reduced to a level of 3.5% (while still maintaining the ratio of emollients set forth in Example 13). It was found that at this lower level of overall emollient, the resulting modified cleansing composition maintained efficacy against makeup removal for all three makeups tested.

Example 13 was prepared, with the modification that dimethicone/trisiloxane at a level of 2% was added. The resulting modified composition as found to improve the skin feel and increase the mascara removal efficacy.

Example 13 was prepared, with the modification that dimethicone was added at a level of 0.5%. the resulting composition was found to improve the skin feel of the composition.

Example 6: Emulsifiers

Various emulsifiers were tested in the formulation, specifically in Example 13. Example 13 was prepared with various emulsifiers, set forth in Table 6 below. The resulting formulations were tested for stability, as well as for makeup removal in vitro and/or in vivo, using the in vitro method set forth in Example 4 above and the in vivo method set forth in Example 1 above.

TABLE 6

Emulsifier Tests

| Emulsifier # | Emulsifier(s) | INCI |
|---|---|---|
| 1A | 1A—ETD2020 + 0.5% Sucrose Cocoate | Acrylates/C10-C30 Alkyl Acrylate Crosspolymer (ETD2020) |
| 1B | 1B—ETD2020 + 0.75% sucrose cocoate | |
| 2 | Ultrez 10 | Carbomer |
| 3 | Aristiflex AVS | Ammonium Acrylyldimethyltaurate/VP Copolymer |
| 4 | ETD2020 + Amphisol K | Acrylates/C10-C30 Alkyl Acrylate Crosspolymer (ETD2020) Cationic single tailed (Amphisol K) |
| 5 | Aristiflex HMB | Ammonium Acryloyldimethyltaurate/Beheneth-25 Methacrylate Crosspolymer |
| 6 | Laponite RD | Laponite RD |
| 7 | ETD2020 + Procetyl AWS (solubilizer) | Acrylates/C10-C30 Alkyl Acrylate Crosspolymer (ETD2020) PPG-5-Ceteth-20 (Procetyl AWS) |
| 8 | Pemulin TR-1 | Acrylates/C10-30 Alkyl Acrylate Crosspolymer |
| 9 | ETD2020 + 0.1% Sucrose Cocoate | Acrylates/C10-C30 Alkyl Acrylate Crosspolymer (ETD2020) |

Emulsifiers 1A and 1B were found to pass formula stability, and gave strong makeup removal as well as passing skin feel evaluation. Emulsifier 2 was found to pass formula stability, but had a weaker makeup removal than Emulsifier 1, and had a least desirable skin feel than Emulsifier 1. Emulsifier 3 did not exhibit stability, as the formula slowly separated. Emulsifier 3 did provide strong skin feel, but exhibited significantly worse makeup removal than Emulsifier 1. Emulsifier 4 failed stability, as it quickly separated. Emulsifier 5 failed stability, as it separated overnight. Emulsifier 6 failed stability, as it quickly separated. Emulsifier 7 passed stability and was deemed the most stable resulting formulation. Emulsifier 7 also passed the skin feel test, but was significantly worse at makeup removal than Emulsifier 1 was. Emulsifier 8 failed stability, as it quickly separated. However, Emulsifier 8 did pass skin feel test, but was not as effective in makeup removal as Emulsifier 1. Emulsifier 9 failed stability, as it separated overnight. Emulsifier 9 was tested for skin feel and passed, however due to lack of stability, Emulsifier 9 was not tested for makeup removal.

The invention claimed is:

1. A cleansing composition comprising a fluid composition comprising:
    a. A cleansing blend comprising a first stearic ester, a second stearic ester, and a branched hydrocarbon, wherein the first stearic ester and second stearic ester are different from each other;
    b. At least one emulsifier;
    c. Water; and
    d. A humectant;
    wherein the first stearic ester, the second stearic ester, and the branched hydrocarbon are present in a weight ratio of about 2:2:1.

2. A cleansing composition comprising a fluid composition comprising:
    a. A cleansing blend comprising a first stearic ester, a second stearic ester, and a branched hydrocarbon, wherein the first stearic ester and second stearic ester are different from each other;
    b. At least one emulsifier;
    c. Water; and
    d. A humectant;
    wherein the first stearic ester, the second stearic ester, and the branched hydrocarbon are present in a weight ratio of from about 1:1:1.3 to about 1:1:1.5.

3. The cleansing composition of claim 1, wherein the first stearic ester comprises an isostearate.

4. The cleansing composition of claim 1, wherein the first stearic ester comprises isopropyl isostearate.

5. The cleansing composition of claim 1, wherein the second stearic ester comprises decyl isostearate.

6. The cleansing composition of claim 1, wherein the second stearic ester comprises highly mono-branched decyl isostearate.

7. The cleansing composition of claim 1, wherein the branched hydrocarbon comprises isohexadecane.

8. A cleansing composition comprising a fluid composition comprising:
    a. A cleansing blend comprising a first stearic ester, a second stearic ester, and a branched hydrocarbon, wherein the first stearic ester and second stearic ester are different from each other;
    b. At least one emulsifier;
    c. Water; and
    d. A humectant;
    wherein the first stearic ester is present in an amount of from about 2.0% to about 4.0% by weight of the fluid composition, the second stearic ester is present in an amount of from about 2.0% to about 4.0% by weight of the fluid composition, and the branched hydrocarbon is present in an amount of from about 2.0% to about 4.0% by weight of the fluid composition.

9. The cleansing composition of claim 1, further comprising a blend of sucrose fatty acid esters.

10. The cleansing composition of claim 9, wherein the blend of sucrose fatty acid esters is present in a combined amount of from about 0.5% to about 1.25% by weight of the fluid composition.

11. The cleansing composition of claim 9, wherein the blend of sucrose fatty acid esters is sucrose cocoate.

12. The cleansing composition of claim 1, wherein the emulsifier is present in an amount of from about 0.1% to about 2.0% by weight of the fluid composition.

13. A cleansing composition comprising a fluid composition comprising:
    a. A cleansing blend comprising a first stearic ester, a second stearic ester, and a branched hydrocarbon, wherein the first stearic ester and second stearic ester are different from each other;
    b. At least one emulsifier;
    c. Water; and
    d. A humectant;
wherein the emulsifier is selected from the group consisting of PEG-6 caprylic/capric glycerides and substituted acrylates.

14. The cleansing composition of claim 1, wherein the emulsifier is a polymeric emulsifier.

15. A method of cleansing the skin of a user, comprising the steps of:
    a. Applying an effective amount of a cleansing composition to a target area of the skin by hand or by use of an applicator, the cleansing composition comprising:
        i. A cleansing blend comprising a first stearic ester, a second stearic ester, and a branched hydrocarbon, wherein the first stearic ester and second stearic ester are different from each other, and wherein the first stearic ester, the second stearic ester, and the branched hydrocarbon are present in a weight ratio of about 2:2:1;
        ii. At least one emulsifier;
        iii. Water; and
        iv. A humectant; and
    b. Rinsing or wiping off the cleansing composition from the target area of the skin.

16. A method of cleansing the skin of a user, comprising the steps of:
    a. Applying an effective amount of a cleansing composition to a target area of the skin by hand or by use of an applicator, the cleansing composition comprising:
        i. A cleansing blend comprising a first stearic ester, a second stearic ester, and a branched hydrocarbon, wherein the first stearic ester and second stearic ester are different from each other, and wherein the first stearic ester, the second stearic ester, and the branched hydrocarbon are present in a weight ratio of from about 1:1:1.3 to about 1:1:1.5;
        ii. At least one emulsifier;
        iii. Water; and
        iv. A humectant; and
    b. Rinsing or wiping off the cleansing composition from the target area of the skin.

17. The cleansing composition of claim 2, wherein the first stearic ester comprises isopropyl isostearate.

18. The cleansing composition of claim 8, wherein the first stearic ester comprises isopropyl isostearate.

19. The cleansing composition of claim 13, wherein the first stearic ester comprises isopropyl isostearate.

20. The method of claim 15, wherein the first stearic ester comprises isopropyl isostearate.

21. The method of claim 16, wherein the first stearic ester comprises isopropyl isostearate.

22. The cleansing composition of claim 2, wherein the second stearic ester comprises decyl isostearate.

23. The cleansing composition of claim 8, wherein the second stearic ester comprises decyl isostearate.

24. The cleansing composition of claim 13, wherein the second stearic ester comprises decyl isostearate.

25. The method of claim 15, wherein the second stearic ester comprises decyl isostearate.

26. The method of claim 16, wherein the second stearic ester comprises decyl isostearate.

27. The cleansing composition of claim 2, wherein the branched hydrocarbon comprises isohexadecane.

28. The cleansing composition of claim 8, wherein the branched hydrocarbon comprises isohexadecane.

29. The cleansing composition of claim 13, wherein the branched hydrocarbon comprises isohexadecane.

30. The method of claim 15, wherein the branched hydrocarbon comprises isohexadecane.

31. The method of claim 16, wherein the branched hydrocarbon comprises isohexadecane.

32. The cleansing composition of claim 2, further comprising a blend of sucrose fatty acid esters.

33. The cleansing composition of claim 8, further comprising a blend of sucrose fatty acid esters.

34. The cleansing composition of claim 13, further comprising a blend of sucrose fatty acid esters.

35. The method of claim 15, further comprising a blend of sucrose fatty acid esters.

36. The method of claim 16, further comprising a blend of sucrose fatty acid esters.

* * * * *